(12) United States Patent
Scattini

(10) Patent No.: US 10,492,382 B2
(45) Date of Patent: Dec. 3, 2019

(54) METHODS FOR THE PRODUCTION OF PERENNIAL ARTICHOKE PLANTS

(71) Applicant: Michael R. Scattini, Salinas, CA (US)

(72) Inventor: Michael R. Scattini, Salinas, CA (US)

(73) Assignee: Luis A. Scattini & Sons, LP, Salinas, CA (US)

( * ) Notice: Subject to any disclaimer, the term of this patent is extended or adjusted under 35 U.S.C. 154(b) by 210 days.

(21) Appl. No.: 15/625,978

(22) Filed: Jun. 16, 2017

(65) Prior Publication Data

US 2017/0359961 A1    Dec. 21, 2017

Related U.S. Application Data

(60) Provisional application No. 62/351,848, filed on Jun. 17, 2016.

(51) Int. Cl.
*A01G 22/00* (2018.01)

(52) U.S. Cl.
CPC ................... *A01G 22/00* (2018.02)

(58) Field of Classification Search
CPC .................................................. A01G 22/00
USPC ........................... 47/58.1 R, 58.1 FV
See application file for complete search history.

(56) References Cited

U.S. PATENT DOCUMENTS

| | | | | |
|---|---|---|---|---|
| 1,758,128 A * | 5/1930 | Rosevear | ............... | A01G 22/00 47/73 |
| 2,069,958 A * | 2/1937 | Diemer Kool | ......... | A01B 1/243 172/21 |
| 2,663,137 A * | 12/1953 | Asbury | ............... | A01D 34/4168 125/3 |
| 2,775,065 A * | 12/1956 | Chepil | ................... | A01H 1/025 47/1.41 |
| 3,645,041 A * | 2/1972 | Addin | ..................... | A01G 17/00 47/58.1 R |
| 4,023,506 A * | 5/1977 | Robey | ................... | E01C 13/083 47/58.1 R |
| 5,060,418 A * | 10/1991 | Pullman | ................... | A01C 1/00 111/100 |
| 9,596,825 B1* | 3/2017 | Peng | ..................... | A01G 22/00 |
| 2006/0242899 A1* | 11/2006 | Parmenter | ................ | A01G 2/00 47/58.1 R |
| 2008/0155890 A1* | 7/2008 | Oyler | ..................... | A01G 22/00 47/1.4 |
| 2010/0083569 A1* | 4/2010 | Danalatos | ................ | C10L 5/363 44/589 |
| 2012/0227122 A1* | 9/2012 | Arrieta | ..................... | A01H 5/02 800/260 |
| 2013/0005569 A1* | 1/2013 | Hendrickson | .......... | C09K 17/22 504/101 |
| 2015/0373927 A1* | 12/2015 | Paans | ................... | A01G 9/1423 47/39 |
| 2016/0242368 A1* | 8/2016 | Levine | ............... | A01G 13/0268 |
| 2016/0255778 A1* | 9/2016 | Redden | .................. | A01G 22/00 |
| 2017/0215353 A1* | 8/2017 | Schurter | ............ | A01G 13/0206 |

FOREIGN PATENT DOCUMENTS

| | | | | |
|---|---|---|---|---|
| CA | 2976783 A1 * | 8/2016 | ............ | A01G 22/00 |
| FR | 3012797 B1 * | 12/2015 | ............ | A01G 22/00 |

OTHER PUBLICATIONS

Bratsch, A. et al. Specialty Crop Profile: Globe Artichoke. Virginia Cooperative Extension Publication 438-108. <http://pubs.ext.vt.edu/438/438-108/438-108_pdf.pdf.> (Year: 2009).*

Acar et al. "Effects of different mowing dates of plant top on tuber yield of Jerusalem artichoke (Helianthus tuberosus L.)" Aug. 17, 2011. African Journal of Biotechnology col. 10(45), pp. 9036-9040. (Year: 2011).*

Bedini et al., "Plant Tissue Cultures from Four Tuscan Globe Artichoke Cultivars", Central European Journal of Biology, vol. 7, No. 4, 2012, pp. 680-689.

Boullani et al., "Improved in Vitro Micropropagation of Artichoke (Cynara Cardunculus Var. Scolymus L.)", European Journal of Scientific Research, vol. 80, No. 4, 2012, pp. 430-436.

Ceccarelli et al., "Globe Artichoke as a Functional Food", Mediterranean Journal of Nutrition and Metabolism, vol. 3, 2010, pp. 197-201.

Iapichino, Giovanni, "Micropropagation of Globe Artichoke (Cynara Cardunculus L. Var. Scolymus)", Chapter 29, Methods in Molecular Biology, vol. 994, 2013, pp. 369-380.

Iapichino, Giovanni, "Micropropagation of Globe Artichoke (Cynara Scolymus L.) from Underground Dormant Buds ("Ovoli")", In Vitro Cellular & Developmental Biology. Plant, vol. 32, Oct.-Dec. 1996, pp. 249-252.

Scattini, Unpublished U.S. Appl. No. 16/370,551, filed Mar. 29, 2019, titled "Artichoke Varieties Named 'PAGA G-1', 'PAGA 13-1', and 'PAGA 15-1'".

(Continued)

*Primary Examiner* — Magdalena Topolski
*Assistant Examiner* — Morgan T Barlow
(74) *Attorney, Agent, or Firm* — Morrison & Foerster LLP

(57) ABSTRACT

The present disclosure relates to methods for the cultivation of perennial artichoke plants. Specifically, the present disclosure relates to methods of cultivating artichoke plants to increase the uniformity and yield of marketable products (e.g. edible mature buds), and to accurately program and condense the harvest interval of artichoke plants grown as perennials in a planting field in order to reduce production and harvesting costs.

15 Claims, 8 Drawing Sheets
(8 of 8 Drawing Sheet(s) Filed in Color)

(56) References Cited

OTHER PUBLICATIONS

Scattini, Unpublished U.S. Appl. No. 16/501,358, filed Mar. 29, 2019, titled "Artichoke Variety Named 'PAGA G-1'".
Scattini, Unpublished U.S. Appl. No. 16/501,354, filed Mar. 29, 2019, titled "Artichoke Variety Named 'PAGA 13-1'".
Scattini, Unpublished U.S. Appl. No. 16/501,352, filed Mar. 29, 2019, titled "Artichoke Variety Named 'PAGA 15-1'".
Smith, "Artichoke Production in California", UC Vegetable Research & Information Center, Publication 7221.

* cited by examiner

METHODS FOR THE PRODUCTION OF PERENNIAL ARTICHOKE PLANTS

CROSS REFERENCE TO RELATED APPLICATIONS

This application claims the benefit of U.S. Prov. App. No. 62/351,848, filed Jun. 17, 2016, which is hereby incorporated by reference in its entirety.

FIELD

The present disclosure relates to methods for the cultivation of perennial artichoke plants. Specifically, the present disclosure relates to methods of cultivating artichoke plants to increase the uniformity and yield of marketable products (e.g. edible mature buds), and to accurately program and condense the harvest schedule of artichoke plants grown as perennials in a planting field.

BACKGROUND

Artichokes (*Cynara cardunculus* var. *scolymus*) are a popular vegetable food source (edible flower bud) in many regions of the world, with nearly 2 million tons of artichokes produced annually by the world's largest artichoke producing countries. Most artichoke cultivation is concentrated in Mediterranean regions, with California being responsible for nearly 100% of all artichoke production in the United States.

Artichokes are true perennials, and perennial-type cultivation methods have been used for traditional artichoke production. In this traditional artichoke production scheme, the artichoke plant is cultivated as a perennial, remaining in the field for multiple years (e.g. 5 to 25 years or more). An example of an artichoke plant historically grown in California using traditional perennial-type cultivation methods is the variety 'Green Globe'. This variety is commonly reproduced from crown. 'Green Globe' is also referred to as an "Heirloom" artichoke.

Artichoke plants cultivated as perennials such as 'Green Globe' are cultivated by traditional, well-known, and labor-intensive techniques. For example, these techniques include using plows to create ditches for winter water flow and harvester walking support. However, the traditional cultivation methods carry a number of challenges. Firstly, for plants cultivated using traditional cultivation methods, there usually exists a significant amount of variability in plant growth and productivity. This plant-to-plant variability reduces the consistency of crop yield and compromises the efficiency of artichoke field management. Secondly, the timing of perennial artichoke bud production using traditional methods is difficult to control. The cropping cycle of artichokes produced as perennials begins when plants are cut back. Traditionally, a cut in May would facilitate a harvest in Fall through Spring of the following year. However, variations in climactic conditions have made it difficult to accurately predict harvest timing, particularly with the onset of global climate change. Other challenges associated with traditional perennial-type artichoke production include the high labor and cost-intensive attributes of this practice, in addition to difficulties with predicting harvest timing and volume. Traditional perennial-type artichoke production also becomes increasingly expensive given that the plants are actively growing eleven months out of each year, and the fields generally require increased maintenance, year over year due to the build-up of pests, weeds and disease. Moreover, perennial cultivation of artichoke is prone to diseases, weeds and pests problems. Traditionally, artichoke is asexually reproduced by division of crown of a plant: rooted sections of the crown (stump) of an artichoke plant are dug out of the ground, split in parts, and transplanted by hand into a new field. This traditional way of asexually reproducing artichokes carries over the contaminating agents, such as pathogens, weed seeds, and insects, associated with the old crown into the new field, which introduces variability into the new field and reduces its yield potential.

As described above, traditional perennial-type artichoke cultivation methods are subject to a number of challenges. However, market demand for artichokes continues throughout the year. In response to year-round demand, as well as the challenges with traditional perennial-type artichoke cultivation methods presented above, artichoke growers and breeding companies have developed seed propagated artichoke varieties. Seed propagated artichokes, also known as seeded artichokes, are commonly referred to as annual artichokes in the industry because they are grown through one harvest interval then destroyed. Seed propagated artichoke plants remain in the field for only e.g. ~5-8 months. In the Castroville, Calif. area, seeded artichoke production typically yields crops of artichokes between May and November. However, seeded artichoke varieties have their own disadvantages. Firstly, they are not typically grown over multiple years (are not grown as perennials), which requires new ground preparation, the purchase of new plants and planting labor, greatly increasing the cost each year. Secondly, the flower buds produced from seeded artichokes are more lignified, with less flavor and tenderness compared to those produced from perennial artichoke plants. The latter attribute is a major reason why food service providers, commercial processors, and consumers still prefer perennial artichoke varieties over annual seeded varieties. Therefore, introduction of annual artichoke does not replace the need for perennial artichokes, and artichoke buds from plants cultivated as perennials remain in high demand.

Accordingly, there exists a need for improved artichoke cultivation methods which produce the high quality buds of perennial-type cultivated artichokes and allow for uniformity in bud production and timing of harvest.

BRIEF SUMMARY

In one aspect, the present disclosure relates to a method of cultivating artichoke plants as perennials, the method including growing artichoke plants in a field on raised beds for more than one harvest interval to produce a field of artichoke plants, wherein the artichoke plants are mowed one or more times per year to stimulate new vegetative growth phases and harvest intervals, and wherein the artichoke plant density in said field is from about 1,700 to about 8,000 artichoke plants per acre.

In some embodiments, the artichoke plants are grown from artichoke crowns. In some embodiments, the artichoke plants are grown from artichoke seed. In some embodiments, the artichoke plants are grown from artichoke plantlets germinated from artichoke seed and germinated in a greenhouse for about 6 weeks. In some embodiments, the artichoke plants are grown from artichoke plantlets regenerated from artichoke tissue culture. In some embodiments, the method further includes growing the artichoke plantlets in greenhouse for about eight weeks in a growth medium comprising peat and vermiculite. In some embodiments, a representative sample of tissue culture has been deposited under ATCC Accession Number X. In some embodiments, the tissue culture is originated from a plant part selected from the group consisting of leaf, anther, pistil, stem, petiole, shoot, shoot tip, root, root tip, fruit, seed, flower, cotyledon, hypocotyl, embryo and meristematic cell. In some embodiments, the tissue culture is originated from a shoot tip of an artichoke plant. In some embodiments, the raised beds have a width from about 40 inches to about 95 inches. In some embodiments, the raised beds have a height from about 2.5 inches to about 30 inches. In some embodiments, the plant spacing between artichoke plants in the raised beds is from about 20 inches to about 50 inches. In some embodiments, the artichoke plants are grown in the field of raised beds for multiple harvest intervals and vegetative growth phases. In some embodiments, the artichoke plants are grown in the field of raised beds from about 8 months to about 20 years. In some embodiments, the artichoke plants are grown in the field of raised beds from about 1.5 years to about 10 years. In some embodiments, the mowing takes place in any month in a year. In some embodiments, the mowing takes place in the fall/autumn for a spring bud production. In some embodiments, the artichoke plants are mowed to 1 inch to 2 feet tall after a harvest interval ends. In some embodiments, artichoke buds are harvested from the artichoke plants grown in the field.

DESCRIPTION OF THE FIGURES

The patent or application file contains at least one drawing executed in color. Copies of this patent or patent application publication with color drawings will be provided by the Office upon request and payment of the necessary fee.

DETAILED DESCRIPTION

Figure 1:
FIG. 1 shows a field that is cultivated using traditional perennial artichoke cultivation methods. This figure illustrates the variability in the field, as well as the infestation of weeds identifiable by the yellow flowers.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Specifically, the present disclosure relates to methods of cultivating artichoke plants to increase the uniformity and yield of marketable products (e.g. edible mature buds), and to accurately program and condense the harvest schedule of artichoke plants grown as perennials in a planting field.

The present disclosure is based, at least in part, on Applicant's development of agricultural techniques to enable year-long production from artichoke plants produced as perennials. Applicant's techniques can be employed to e.g. reduce maintenance in perennial artichoke fields, reduce the associated costs, reduce the harvesting labor costs, increase the artichoke plants per acre, increase annual artichoke bud yield, and increase the phenotypic uniformity of artichoke plants, particularly with respect to uniformity in bud production and timing.

Accordingly, provided herein are methods of cultivating artichoke plants as perennials such that the artichoke plants produce high yields and exhibit uniform bud production with harvest times that may also be accurately controlled or predicted.

It is to be understood that one, some, or all of the properties of the various embodiments described herein may be combined to form other embodiments of the present disclosure. These and other aspects of the present disclosure will become apparent to one of skill in the art. These and other embodiments of the present disclosure are further described by the detailed description that follows.

Definitions

In the description that follows, a number of terms are used. In order to provide a clear and consistent understanding of the specification and claims, including the scope to be given such terms, the following definitions are provided.

As used herein, the term "asexual propagation" or "vegetative reproduction" refers to process by which new organisms arise without production of seeds or spores. It can occur naturally or be induced artificially. Types of asexual propagation include division, cutting, vegetative apomixis, layering, budding, grafting and tissue culture.

As used herein, the term "division" or "splitting" is a method of asexual plant propagation, by which the plant (usually an herbaceous perennial) is broken up into two or more parts. Both the root and crown of each part are kept intact on which new plants are formed. Division of crown or crown is a traditional technique for perennial artichoke propagation.

As used herein, the term "crown" is the root-stem junction of a plant. When used in the context of asexual propagation, it can be used interchangeably with the term "rootstock" and refer to a rhizome cluster, which can be divided into smaller pieces as a way to asexually propagate a plant.

As used herein, the term "plant tissue culture" or simply "tissue culture" is a collection of techniques used to maintain or grow plant cells, tissues or organs under sterile conditions on a nutrient culture medium of known composition. In modern agriculture, plant tissue culture is used to rapidly multiplying stock plant material to produce a large number of progeny plants, a practice also known as "micropropagation".

As used herein, the term "perennial plant" or simply "perennial" is a plant is maintained through multiple harvest intervals. In warmer and more favorable climates, perennials grow continuously. In seasonal climates, their growth is limited to the growing season.

As used herein, the term "annual plant" or simply "annual" is a plant that completes its life cycle, from germination to the production of seed, within one year, and then is destroyed. In artichoke production, annual crops have to be re-planted after each harvest interval.

As used herein, the term "mowing", "chopping", "cutting", or "cutting back" refers to any mechanical or manual process by which the vegetative portion of the plant is removed leaving plant material above ground to a height of about one inch to about two feet tall. Mowing stimulates the artichoke plant to reinvigorate and enter another vegetative growth phase.

As used herein, the term "production interval" refers to the time frame lasting from the initial planting of the artichoke plants in an artichoke production field to the removal of the artichoke plants from the production field and/or the destruction of the artichoke plants in the field. For annual artichokes, the production interval includes only one harvest interval and one vegetative growth phase which means the plant's production interval is less than a year (e.g. 5 to 8 months). For perennial artichokes, the production interval typically lasts for more than one year in duration such that the production interval includes multiple harvest intervals and multiple vegetative growth phases.

As used herein, the term "harvest interval" refers to the time frame lasting from the harvest of the first marketable product from a field to the mowing down of the plants to start a new vegetative growth phase; or the destruction of the plants at the end of the production interval. A harvest interval will include several harvest events in which a labor force will enter the production field to harvest the mature marketable products.

As used herein, the term "vegetative growth phase" refers to the time frame between planting new plants or mowing existing plants to the first day of the harvest interval.

As used herein, the term "contaminating agents" refers to those agents which, if planted with an artichoke plant, may decrease the vigor of the artichoke plant (e.g. via insect and/or weed competition).

As used herein, a "substantially clean" artichoke plant refers to an artichoke plant that is substantially free of contaminating agents normally present in artichoke production fields (e.g. weed seeds, insects, slugs, etc.). For example, a substantially clean artichoke plant may be in association with less than 30%, less than 20%, less than 10%, less than 5%, less than 2.5%, and more preferably 1% or less (by weight) contaminating agents.

As used herein, the term "harvestable products" refers to the various plant parts that may be obtained from artichoke plants cultivated according to the methods of the present disclosure. For example, a harvestable product may be an artichoke flower bud before the flower comes into bloom, which is the portion of artichoke plants commonly used for human consumption. Harvestable products may also include, for example, seeds, roots, leaves, flowers, or other portions of plants.

The use of the terms "a," "an," and "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments of the disclosure and does not pose a limitation on the scope of the disclosure unless otherwise claimed. No language in the specification should be construed as indicating any non-claimed element as essential to the practice of the embodiments of the disclosure.

Reference to "approximately" or "about" a value or parameter herein refers to the usual error range for the respective value readily known to the skilled person in this technical field. Reference to "about" or "approximately" a value or parameter herein includes (and describes) aspects that are directed to that value or parameter per se. For example, description referring to "about X" includes description of "X".

It is understood that aspects and embodiments of the present disclosure described herein include "comprising," "consisting," and "consisting essentially of" aspects and embodiments.

As used herein, the term "plant" includes plant cells, plant protoplasts, plant cell tissue cultures from which artichoke plants can be regenerated, plant calli, plant clumps and plant cells that are intact in plants or parts of plants, such as fruit, leaves, pollen, embryos, cotyledons, hypocotyl, roots, root tips, anthers, pistils, flowers, seeds, stems and the like.

Artichoke Plants

The botanical classification of artichokes is *Cynara cardunculus* var. *scolymus*. The portions of artichoke plants that are commonly used for human consumption are the flower buds before coming into bloom. Artichoke plants are well-known to one of skill in the art.

Traditional methods of artichoke cultivation have involved growing artichoke plants as perennials. For example, artichokes plants that have been asexually propagated (e.g. vegetative propagation), planted in a field, and grown for multiple years are artichoke plants that are grown as perennials. An artichoke variety that is commonly grown as a perennial is the 'Green Globe' variety. Traditionally cultivated perennial artichoke plants are not grown on raised beds in an artichoke planting field, but are planted in flat fields with winter drainage ditches that are generally installed during the fall/autumn months.

Growing artichoke varieties as annuals began to gain traction in the 1980s as seed-based artichoke varieties were developed. Artichokes grown as annuals are typically planted as seeds and remain in the planting field for one growing season (e.g. 5 to 8 months). While artichokes grown as annuals may produce higher yields in a single year than artichokes grown as perennials, annual artichokes are not grown for more than one year.

It is an object of the present disclosure to provide methods of cultivating artichokes as perennials (using same plant over multiple calendar years) such that the artichoke plants produce high yields and exhibit uniform bud production with harvest times that may also be accurately controlled or predicted.

Certain aspects of the present disclosure relate to growing substantially clean artichoke plants over a production interval, where the artichoke plants are suitable for harvesting artichoke buds or other harvestable products.

Artichoke plants of the present disclosure should be suitable for planting in an artichoke production field and should be suitable for production of artichoke buds. Artichoke plants of the present disclosure may include, for example, various artichoke plants or parts thereof at various stages of development. For example, an artichoke plant may include seeds, seedlings, callus tissue, crowns, sporophytes, whole plants, and various groups of plant cells organized into structural and/or functional units. In some embodiments, artichoke plants are whole plants with root and aerial leaf tissues.

Substantially clean artichoke plants may be prepared by various methods. For example, an artichoke plant may be grown for a period under controlled conditions in a greenhouse that is sterile or semi-sterile. These substantially clean artichoke seedlings may then be planted into an artichoke field. In some embodiments, a substantially clean artichoke plant is a substantially clean artichoke seed. In some embodiments, substantially clean artichoke plants are produced from artichoke tissue culture to give rise to artichoke plantlets. In some embodiments, substantially clean artichoke plants are produced from existing artichoke plant crowns that have been removed from production fields and cleaned prior to replanting. Artichoke plantlets produced from tissue culture may also be grown for a period under controlled conditions in e.g. a greenhouse that is sterile or semi-sterile. Methods of using tissue culture to regenerate artichoke plants are well-known in the art. Tissue culture propagation is a method of asexual reproduction of plant material. Plants are reproduced under sterile conditions by placing a small portion of a mother plant (e.g. an explant) on a nutrient culture medium of known composition. Tissue culture is widely used to produce clones of a plant.

Various tissue culture methods may be used to generate substantially clean artichoke plants of the present disclosure. Tissue culture, also known as micropropagation, is a propagation method used to produce plants under sterile conditions. This method uses plant explants that have been sterilized before being placed in containers with a growing medium that has nutrients added. The explants, the containers and the medium have all been sterilized, and this prevents any cut or torn tissue, or the entire explant itself, from becoming infected with a microorganism during the time these plant parts require to become rooted or to multiply. Using plant tissue, it is possible to grow exact copies of the donor plant. Tissue culture thus involves the in vitro initiation of plant culture, propagation, and rooting under controlled environmental conditions and may be used for ex vitro establishment of plant propagules in the soil. An exemplary tissue culture method that may be used herein involves the following steps: 1) establishment of an aseptic (sterile) culture; 2) multiplication of propagules; 3) preparation of propagules for successful transfer to soil (rooting and "hardening"); and 4) establishment of propagules in soil (or other appropriate growing medium). Plants obtained as the product of tissue culture propagation may be referred to as regenerated plants.

Various harvestable products may be obtained from artichoke plants cultivated according to the methods of the present disclosure. For example, a harvestable product may be an artichoke flower bud before the flower comes into bloom, which is the portion of artichoke plants commonly used for human consumption. Harvestable products may also include, for example, seeds, roots, leaves, flowers, or other portions of plants.

The artichoke cultivation methods of the present disclosure may be useful for increasing harvestable artichoke bud yield. The USDA provides guidelines for assigning artichoke bud grades. Grades include U.S. No. 1 and U.S. No. 2, based primarily on external appearance. Buds are classified by the number that fit into a standard carton of about 10 kg (23 pounds/lbs.). For example, a size 18 bud means 18 buds per carton (also referred to as "18s"). Standard grades include 18s (>13 cm diameter, 5.4 inches), 24s (10 to 13 cm, 4.0 to 4.5 inches), 36s (8.5 to 10 cm, 3.5 to 4.0 inches), 48s (7.5 to 8.5 cm, 3.0 to 3.5 inches) or 60s (6.5 to 7.5 cm, 2.75 to 3 inches) buds per carton. Buds may also be characterized as a size 12, which equates to a size of between 13-15 inches in circumference. The methods of the present disclosure may be used to increase the number of size 12 artichokes harvested from an artichoke production field. Size 12 artichokes may represent at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% or more of the total harvested buds from an artichoke production field during a given harvesting event.

Artichoke Propagation

Propagation of artichoke plants can occur in a number of ways.

Crown

Traditionally, artichoke is asexually reproduced by division of crown (where the plant stem meets the roots) of a plant: the roots and crown of an artichoke plant is dug out of the ground, split in parts, and then transplanted into a new field. This traditional way of asexually reproducing artichokes brings the diseases and pests associated with old crowns into the new field, which significantly decreases yield and increases field management costs.

Seed

Alternatively, artichoke can be sexually reproduced by seed. Typically, seed propagated artichoke plants remain in the field for only e.g. ~5-8 months. In the Castroville, Calif. area, seeded artichoke production typically yields crops of artichokes between May and November.

Tissue Culture

Another way of propagating artichokes is to use tissue culture techniques. Tissue culture techniques have a number of advantages over traditional methods of propagation, including being able to quickly produce a large number of plantlets, plantlets are amenable to transplanting by machine, regenerated plants are robust and disease-free, etc. Plant tissue culture refers to the various methods which have been developed for asexually reproducing plants from juvenile and rejuvenated mature plant material. Typically, a shoot, shoot tip, bud, stem section, or stem base is excised from a growing plant, disinfested, and placed in appropriate hormone and nutrient solutions to cause auxillary growth and shoot lengthening in a multiplication culture to form multiple plant propagules. Initial plantlets regenerated from tissue culture in a well-controlled laboratory environment are usually too fragile for direct field growth. In order to acclimatize them into field conditions, plantlets are usually first grown in a greenhouse before they are transplanted into an open field. Techniques of tissue culture are known in the art. For example, reference may be had to El Boullani, et al., European Journal of Scientific Research. 2012, 80: 4, 1450-

216, Iapichino, et al., In Vitro Cell. Dev. Biol.-Plant. 1996, 32: 249, and Bedini, et al., Open Life Sciences. 2012, 7: 4, 680-689.

Artichoke Planting and Cultivation

Certain aspects of the present disclosure relate to growing substantially clean artichoke plants over a production interval, where the artichoke plants are suitable for harvesting an artichoke bud or other harvestable product. Further, the artichoke planting and cultivation methods as described herein may allow for the production of artichoke plants as perennials (using same plant over multiple calendar years) such that the artichoke plants produce high yields and exhibit uniform bud production with harvest times that may also be accurately controlled or predicted. The artichoke planting and cultivation methods used to achieve the above are described herein.

Ground Preparation

The field for planting artichoke plants of the present disclosure may have its ground prepared in a number of ways. For example, ground preparation may involve deep tillage, as well as several disking, chiseling, and lilliston passes (Lilliston cultivators). General methods for artichoke field ground preparation are known in the art and will be readily apparent to the skilled artisan in view of the present disclosure.

Bed Preparation

Bed preparation in artichoke production fields prepared according to the methods of the present disclosure involves the use of raised beds. Raised beds in artichoke fields as described herein are prepared such that the soil for planting is raised above the surrounding field soil height. This is in contrast to e.g. traditional perennial-type artichoke cultivation methods where there is no bed preparation; the artichokes are planted on flat ground and a grid pattern is created to mark plant spacing.

Raised beds in artichoke production fields prepared according to the methods of the present disclosure may have varying heights. Raised beds may have a height of, for example, at least 2.5 inches, at least 5 inches, at least 7.5 inches, at least 10 inches, at least 12.5 inches, at least 15 inches, at least 17.5 inches, at least 20 inches, at least 22.5 inches, at least 25 inches, at least 27.5 inches, at least 30 inches, at least 32.5 inches, at least 35 inches, at least 37.5 inches, or at least 40 inches. Raised beds may have a height of, for example, between 2.5-5 inches, between 5-10 inches, between 5-15 inches, between 5-20 inches, between 5-20 inches, between 5-25 inches, between 5-30 inches, between 10-15 inches, between 10-17.5 inches, between 10-20 inches, between 10-25 inches, between 10-30 inches, between 15-20 inches, between 15-25 inches, between 15-30 inches, between 17.5-25 inches, between 17.5-30 inches, between 20-25 inches, between 20-30 inches, or between 25-30 inches.

Raised beds in artichoke production fields prepared according to the methods of the present disclosure may have varying widths. Raised beds may have a width of, for example, at least 40 inches, at least 50 inches, at least 55 inches, at least 60 inches, at least 65 inches, at least 70 inches, at least 75 inches, at least 80 inches, at least 85 inches, at least 90 inches, at least 95 inches, or at least 100 inches. Raised beds may have a width of, for example, between 40-50 inches, between 40-55 inches, between 40-60 inches, between 40-65 inches, between 40-70 inches, between 40-75 inches, between 40-80 inches, between 40-85 inches, between 40-90 inches, between 40-95 inches, between 40-100 inches, between 50-60 inches, between 50-65 inches, between 50-70 inches, between 50-75 inches, between 50-80 inches, between 50-85 inches, between 50-90 inches, between 50-95 inches, between 50-100 inches, between 60-70 inches, between 60-75 inches, between 60-80 inches, between 60-85 inches, between 60-90 inches, between 60-95 inches, between 60-100 inches, between 65-70 inches, between 65-75 inches, between 65-80 inches, between 65-85 inches, between 65-90 inches, between 65-95 inches, between 65-100 inches, between 70-75 inches, between 70-80 inches, between 70-85 inches, between 70-90 inches, between 70-95 inches, between 70-100 inches, between 75-80 inches, between 75-85 inches, between 75-90 inches, between 75-95 inches, between 75-100 inches, between 80-85 inches, between 80-90 inches, between 80-95 inches, between 80-100 inches, between 85-90 inches, between 85-95 inches, between 85-100 inches, or between 90-95.

Plant Source

As described herein, artichoke plants may be grown from various sources in the improved perennial artichoke cultivation methods. In some embodiments, the artichoke plants are grown from artichoke crowns. In some embodiments, the artichoke plants are grown directly from artichoke seed. In some embodiments, the artichoke plants are grown from artichoke plantlets that are germinated from artichoke seed. In some embodiments, the artichoke plants are grown from artichoke plantlets that are regenerated from artichoke tissue culture.

Planting and Plants Per Acre

Artichoke plants of the present disclosure may be planted in artichoke fields in a variety of ways. For example, artichoke plants may be mechanically transplanted into the field. Artichoke plant spacing in a row may also vary. For example, in row plant spacing may be at least 20 inches, at least 25 inches, at least 30 inches, at least 35 inches, at least 40 inches, at least 45 inches, at least 50 inches, at least 55 inches, or at least 60 inches. In row plant spacing may be, for example, between 15-20 inches, between 15-25 inches, between 15-30 inches, between 15-35 inches, between 15-40 inches, between 15-50 inches, between 15-60 inches, between 20-25 inches, between 20-30 inches, between 20-35 inches, between 20-40 inches, between 20-45 inches, between 20-50 inches, between 20-55 inches, between 20-60 inches, between 25-30 inches, between 25-35 inches, between 25-40 inches, between 25-45 inches, between 25-50 inches, between 25-55 inches, between 25-60 inches, between 30-35 inches, between 30-40 inches, between 30-45 inches, between 30-50 inches, between 30-55 inches, between 30-60 inches, between 35-40 inches, between 35-45 inches, between 35-50 inches, between 35-55 inches, between 35-60 inches, between 40-45 inches, or between 40-50 inches. The artichoke plant spacing as described herein is in contrast to e.g. traditional perennial-type artichoke cultivation methods where there is typically 9-10 feet spacing and 3-4.5 feet in row spacing. The spacing methods described herein allow for substantially more artichoke plants to be planted per acre as compared to e.g. traditional perennial-type artichoke cultivation methods.

The number of artichoke plants that may be grown per acre according to the methods of the present disclosure may vary. The number of artichoke plants per acre may be, for example, at least 1,700 plants/acre, at least 2,000 plants/acre, at least 2,250 plants/acre, at least 2,500 plants/acre, at least 2,750 plants/acre, at least 3,000 plants/acre, at least 3,250 plants/acre, at least 3,500 plants/acre, at least 4,000 plants/acre, at least 4,500 plants/acre, at least 5,000 plants/acre, at least 5,500 plants/acre, at least 6,000 plants/acre, at least 6,500 plants/acre, at least 7,000 plants/acre, at least 7,500 plants/acre, or at least 8,000. The number of artichoke plants per acre may be, for example, between 1,500-2,000 plants/acre, between 1,500-2,250 plants/acre, between 1,500-2,500 plants/acre, between 1,500-2,750, between 1,500-3,000 plants/acre, between 1,500-3,250 plants/acre, between 1,500-3,500 plants/acre, between 1,500-3,750 plants/acre, between 1,500-4,000 plants/acre, between 1,600-2,000 plants/acre, between 1,600-2,500 plants/acre, between 1,600-3,000 plants/acre, between 1,600-3,500 plants/acre, between 1,600-4,000 plants/acre, between 1,700-2,000 plants/acre, between 1,700-2,500 plants/acre, between 1,700-3,000 plants/acre, between 1,700-3,500 plants/acre, between 1,700-4,000 plants/acre,1,750-2,000 plants/acre, between 1,750-2,250 plants/acre, between 1,750-2,500 plants/acre, between 1,750-2,750, between 1,750-3,000 plants/acre, between 1,750-3,250 plants/acre, between 1,750-3,500 plants/acre, between 1,750-3,750 plants/acre, between 1,750-4,000 plants/acre, between 2,000-2,250 plants/acre, between 2,000-2,500 plants/acre, between 2,000-2,750, between 2,000-3,000 plants/acre, between 2,000-3,250 plants/acre, between 2,000-3,500 plants/acre, between 2,000-3,750 plants/acre, between 2,000-4,000 plants/acre, between 2,500-2,750, between 2,500-3,000 plants/acre, between 2,500-3,250 plants/acre, between 2,500-3,500 plants/acre, between 2,500-3,750 plants/acre, between 2,500-4,000 plants/acre, between 2,750-3,000 plants/acre, between 2,750-3,250 plants/acre, between 2,750-3,500 plants/acre, between 2,750-3,750 plants/acre, between 2,750-4,000 plants/acre, between 3,000-3,250 plants/acre, between 3,000-3,500 plants/acre, between 3,000-3,750 plants/acre, between 3,000-4,000 plants/acre, between 3,000-5,000 plants/acre, between 3,000-6,000 plants/acre, between 3,000-7,000 plants/acre, between 3,000-8,000 plants/acre, between 3,000-9,000 plants/acre, between 4,000-5,000 plants/acre, between 4,000-6,000 plants/acre, between 4,000-7,000 plants/acre, between 4,000-8,000 plants/acre, between 4,000-9,000 plants/acre, between 5,000-6,000 plants/acre, between 5,000-7,000 plants/acre, between 5,000-8,000 plants/acre, between 6,000-7,000 plants/acre, between 6,000-8,000 plants/acre, or between 7,000-8,000 plants/acre. The artichoke planting methods and plants/acre as described herein are in contrast to e.g. traditional perennial-type artichoke cultivation methods, which are typically planted to accommodate ~950-1,700 artichoke plants/acre. The spacing methods described herein allow for substantially more artichoke plants to be planted per acre as compared to e.g. traditional perennial-type artichoke cultivation methods.

Artichoke Field Maintenance

The methods of the present disclosure allow for substantially reduced labor and costs associated with maintenance of artichoke fields. This is in contrast to e.g. traditional perennial-type artichoke cultivation methods which typically incur extensive costs associated with labor and materials for maintaining artichoke fields.

Various fertilization schemes may be used in artichoke planting fields of the present disclosure. Fertilizer compositions and methods for fertilizing artichoke fields are well-known in the art. Fertilization schemes may include, for example, soil amendments before artichoke planting if needed, early side dressing with a tractor, and fertilization by sprinkler or drip systems. Irrigation of the planting field may also be achieved via drip, sprinkler, or furrow.

Maintenance of contaminating agents (e.g. weeds, pests, insects, etc.) in artichoke planting fields of the present disclosure may be managed as needed. This includes e.g. pesticide spraying, slug and snail control, and mice or gopher control. However, the artichoke planting methods of the present disclosure should allow for substantially reduced field maintenance costs and labor as compared to e.g. traditional perennial-type artichoke cultivation methods. This is because traditional perennial-type artichoke cultivation methods facilitate weed, pest, insects, etc. buildup over years given the nature of these methods. The use of a substantially clean artichoke plant source, as well as the effective plant alignment on raised beds as described herein, should contribute to cost and labor savings associated with maintenance of artichoke planting fields.

Artichoke planting fields may be weeded as needed, although it is thought that the effective bed width and space used in the methods of the present disclosure should substantially reduce the needed for weeding as compared to e.g. traditional perennial-type artichoke cultivation methods. Weeding refers to the removal of unwanted weed plants from an artichoke field. This may be performed manually with e.g. a hoe or shovel, machinery, and by the use of chemical herbicides. Further, methods to remove weeds may be performed manually by hand or with the aid of machinery.

Stumping practices in artichoke planting fields of the present disclosure does not need to be practiced. Stumping refers to the labor-intensive agricultural practice of manually removing old bud bearing stems of a perennial artichoke plant. The practice involves forcing a long metal bar, stumping knife, axe, or stalk knife into the interior of the plant, and removing these old bearing stems, at ground level. Once removed, the stumps must be incorporated into the soil using a tractor pulling a rotovator. The purpose is the increase future yield of artichokes. This occurs by forcing the plant to produce a new bud-producing stem in its place. Stumping and rotovating are a common practices in e.g. traditional perennial-type artichoke cultivation methods. However, the artichoke cultivation methods as described herein remove the need for stumping and rotovating.

The artichoke planting and cultivation methods of the present disclosure may also allow for the artichoke field to be grown organically and certified as such. Organic farming methods are well-known to those of skill in the art.

Winter Preparation

Artichoke planting fields of the present disclosure may be prepared for the winter season. Such winter preparation may include, for example, installing tail ditches at the low ends of the fields to capture and direct the flow of furrow water out and away from the field and the plants. No plows are required for this process. This is in contrast to e.g. traditional perennial-type artichoke cultivation methods, where plows are repeatedly passed through the field to create a ditch for the water to flow and harvesters to walk on. Tail ditches are then installed at the low ends of the fields to capture and direct the flow out and away from the field and plants. In the spring following winter rains, the ditches must be closed and the soil leveled in the field.

Production Timing

The artichoke planting and cultivation methods as described herein may allow for the production of artichoke plants as perennials (using same plant over multiple harvest intervals) such that the artichoke plants produce high yields and exhibit uniform bud production with harvest times that may also be accurately controlled or predicted resulting in a compressed harvest interval which in turn may reduce harvesting labor costs.

The uniform artichoke bud production associated with the artichoke cultivation methods of the present disclosure allow for controlled timing of artichoke bud production and subsequent harvest. For example, chopping of artichokes in a uniform production field may be used to control production and harvest time. In the methods described herein, chopping may involve removing the bulk of vegetative growth of an artichoke plant, leaving plants at a height of approximately 1 inch to 2 feet tall. Artichoke plants that have been chopped in this manner will initiate a new vegetative growth phase and subsequent harvest interval. The timing of chopping a uniform artichoke production field can thus be used to predict the timing of when the new round of artichoke growth will be ready for production and harvest.

Chopping of artichoke plants cultivated according to the methods described herein may be performed one or more times during a single calendar year. Artichoke plants may be chopped, for example, at least one time, at least two times, at least three times, at least four times, at least five times, at least six times, at least seven times, at least eight times, at least nine times, or 10 or more times during a single calendar year. Artichoke plants may be chopped, for example, between 1-2 times, between 1-3 times, between 1-4 times, between 1-5 times, between 1-6 times, between 1-7 times, between 1-8 times, between 1-9 times, between 1-10 times, between 2-3 times, between 2-4 times, between 2-5 times, between 2-7 times, between 2-10 times, between 3-5 times, between 3-7 times, between 3-10 times, between 5-7 times, between 5-10 times, or between 7-10 times or more in a single calendar year.

Artichoke plants grown according to the methods described herein may be chopped or planted in e.g. the fall for a spring harvest. The artichoke plants may be chopped at various times throughout the year to control bud production timing. These methods allow for relatively easy scheduling of artichoke production. This is in contrast to e.g. traditional perennial-type artichoke cultivation methods, where it is very difficult to schedule a harvest. Generally, these traditional methods involve chopping the plants in May for a fall and spring harvest, and/or a chopping in November for a June/July harvest. The stringency in timing associated with traditional methods makes it difficult to control harvest time. This is exacerbated by the relative non-uniformity of bud production of artichoke plants cultivated as perennials by traditional methods. Timing a harvest is difficult when bud production across a field is asynchronous.

As described above, for a particular artichoke variety, the artichoke plants of that variety cultivated according to the methods described herein exhibit substantially uniform phenotypic characteristics, particularly with respect to uniformity in the timing of bud production. The uniformity of phenotypic characteristics may refer to various traits of interest in artichoke production. In some embodiments, the uniformity refers to the harvest time of the artichoke plants being the same or identical. In some embodiments, the uniformity refers to the quality of harvestable products being the same or identical.

Uniformity may be measured by e.g. quantifying the number of plants in a population that exhibit uniform characteristics with respect to the total number of plants in the population. In some embodiments, the total population of plants is the total number of artichoke plants grown in an artichoke production field being assayed for uniformity. The quantity of uniform plants in a population may be represented as a percentage or ratio of total plants in the population measured for uniformity. Artichoke plants exhibiting a substantially uniform phenotypic characteristic (e.g. uniform bud production) may be at least 75%, at least 80%, at least 85%, at least 90%, at least 95%, at least 99%, or 100% of the total number of plants in the population. Artichoke plants exhibiting a substantially uniform phenotypic characteristic (e.g. uniform bud production) may be between 75-80%, between 75-85%, between 75-90%, between 75-95%, between 75-100%, between 80-85%, between 80-90%, between 80-95%, between 80-100%, between 85-90%, between 85-95%, between 85-100%, between 90-95%, between 90-100%, or between 95-100% of the total number of plants in the population.

Harvesting

The methods of the present disclosure may allow for fewer artichoke harvest events during a harvest interval as compared to traditional perennial-type artichoke cultivation methods. In perennial artichoke planting fields cultivated using traditional methods, artichoke production is varied given the non-uniformity of artichoke bud maturation that occurs using these traditional methods. As a result, artichoke harvesting typically occurs many different times throughout the year depending on weather patterns and disease and pest pressure. In contrast, the uniform bud production that occurs using the methods as described herein allows for better control of artichoke production and thus harvest timing may be more accurately predicted. This may lead to fewer artichoke harvest events per harvest interval given the uniformity of artichoke bud production.

Products may be harvested from artichoke plants cultivated according to the methods of the present disclosure at various times during a harvest cycle. Harvested products may be harvested, for example, at least 1 time, at least 2 times, at least 3 times, at least 4 times, at least 5 times, at least 6 times, at least 7 times, at least 8 times, at least 9 times, at least 10 times, at least 11 times, at least 12 times, at least 13 times, at least 14 times, or at least 15 times in a single harvest cycle. Harvested products may be harvested, for example, between 2-10 times, between 5-10 times, between 7-10 times, between 5-15 times, between 7-15 times, or between 10-15 times in a single harvest cycle contrasted with 20 to 30 events in a tradition perennial field.

The production interval for growing and harvesting artichoke plants and/or products thereof according to the methods of the present disclosure may be more than one year in duration. The production interval refers to the time frame lasting from the initial planting of the artichoke plants in an artichoke production field to the removal of the artichoke plants from the production field and/or the destruction of the artichoke plants in the field. Generally, the production interval includes more than one harvest interval such that the artichoke plants are not grown as annuals. The production interval may be, for example, at least one year, at least two years, at least three years, at least four years, at least five years, at least six years, at least seven years, at least eight years, at least nine years, at least ten years, at least 12 years, at least 15 years, at least 17 years, or at least 20 years. The production interval may be, for example, between 1.5-2 years, between 1.5-3 years, between 1.5-4 years, between 1.5-5 years, between 1.5-6 years, between 1.5-7 years, between 1.5-8 years, between 1.5-9 years, between 1.5-10 years, between 2-3 years, between 2-4 years, between 2-5 years, between 2-6 years, between 2-7 years, between 2-8 years, between 2-9 years, between 2-10 years, between 3-4 years, between 3-5 years, between 3-6 years, between 3-7 years, between 3-8 years, between 3-9 years, between 3-10 years, between 3-15 years, between 4-5 years, between 4-6 years, between 4-10 years, between 5-10 years, between 5-12 years, between 6-7 years, between 6-8 years, between 6-9 years, between 6-10 years, between 8-10 years, between 1-15 years, between 1-20 years, between 5-15 years, between 5-17 years, between 5-20 years, between 10-15 years, or between 10-20 years.

As described above, the artichoke planting methods of the present disclosure may be used to increase the yield of a harvested artichoke product. The harvested product may include e.g. harvested artichoke buds. Yield of harvested products may be expressed as units where e.g. one standard carton of artichoke buds equals one harvested unit. A standard carton of artichoke buds is about 10 kg, or 23 lbs/pounds in weight. The yield of a harvested artichoke product may be, for example, at least 500 units, at least 550 units, at least 600 units, at least 650 units, at least 700 units, at least 750 units, at least 800 units, at least 850 units, at least 900 units, at least 950 units, at least 1,000 units, at least 1,050 units, at least 1,100 units, at least 1,150 units, at least 1,200 units, at least 1,250 units, at least 1,300 units, at least 1,350 units, at least 1,400 units, at least 1,450 units, at least 1,500 units, at least 1,550 units, at least 1,600 units, at least 1,650 units, at least 1,700 units, at least 1,750 units, at least 1,800 units, at least 1,850 units, at least 1,900 units, at least 1,950 units, or at least 2,000 units. The yield of a harvested artichoke product may be, for example, between 500-600 units, between 500-700 units, between 500-800 units, between 500-900 units, between 500-1,000 units, between 500-1,100 units, between 500-1,200 units, between 500-1,300 units, between 500-1,400 units, between 500-1,500 units, between 500-1,600 units, between 600-700 units, between 600-800 units, between 600-900 units, between 600-1,000 units, between 600-1,100 units, between 600-1,200 units, between 600-1,300 units, between 600-1,400 units, between 600-1,500 units, between 600-1,600 units, between 700-800 units, between 700-900 units, between 700-1,000 units, between 700-1,100 units, between 700-1,200 units, between 700-1,300 units, between 700-1,400 units, between 700-1,500 units, between 700-1,600 units, between 800-900 units, between 800-1,000 units, between 800-1,100 units, between 800-1,200 units, between 800-1,300 units, between 800-1,400 units, between 800-1,500 units, between 800-1,600 units, between 900-1,000 units, between 900-1,100 units, between 900-1,200 units, between 900-1,300 units, between 900-1,400 units, between 900-1,500 units, between 900-1,600 units, between 1,000-1,100 units, between 1,000-1,200 units, between 1,000-1,300 units, between 1,000-1,400 units, between 1,000-1,500 units, between 1,000-1,600 units, between 1,100-1,200 units, between 1,100-1,300 units, between 1,100-1,400 units, between 1,100-1,500 units, between 1,100-1,600 units, between 1,200-1,300 units, between 1,200-1,400 units, between 1,200-1,500 units, between 1,200-1,600 units, between 1,300-1,400 units, between 1,300-1,500 units, between 1,300-1,600 units, between 1,400-1,500 units, between 1,400-1,600 units, or between 1,500-1,600 units. The yield obtained with the methods described herein is in contrast to e.g. traditional perennial-type artichoke cultivation methods which typically produce yields of 300-600 units, where one unit is a standard carton of harvested artichoke buds weighing about 10 kg, or 23 lbs/pounds. One of skill would understand that yield and production may be impacted by various factors such as e.g. pest damage, frost, air/soil temperatures, etc.

Post-Harvest Plant Maintenance

Various post-harvest plant maintenance practices may be practiced in artichoke fields according to the methods of the present disclosure. Such practices may involve field mowing. For example, as long as the field and plant conditions are favorable, the plants can be mowed to 1 inch to 2 feet tall after each harvest cycle ends, and possibly again during vegetative growth phases in order to start a new growth cycle and influence the timing of bud development. Such post-harvest maintenance practices are in contrast to e.g. traditional perennial-type artichoke cultivation methods which commonly use post-harvest knifing techniques. Knifing commonly occurs in traditional perennial-type artichoke cultivation methods after chopping artichoke plants, where chopping typically involves removing the bulk of vegetative growth of an artichoke plant, leaving plants at a height of approximately 6 to 24 inches. After chopping, a tool with a sharp blade oriented parallel to the ground is used to cut artichoke plants under the surface approximately 1 to 6 inches deep. This cut is made to the crown of the plant. Debris from this technique is pushed away from the crown to be mixed into the field soil. Remaining roots and crown from these "knifed" plants begin to grow and start a new cycle.

The post-harvest plant maintenance practices of the present disclosure are also in contrast to e.g. practices where artichokes are grown as annuals. In these annual practices, plants and root systems are commonly disked into the soil.

EXAMPLES

The following examples are offered for illustrative purposes and to aid one of skill in better understanding the various embodiments of the disclosure. The following examples are not intended to limit the scope of the present disclosure in any way.

Example 1

Crown-propagated Artichoke Planting and Cultivation Method

This example demonstrates a crown-propagated artichoke planting and cultivation method that may be used to provide better control of artichoke production in a calendar year, as well as allow for continued artichoke production across multiple years.

Traditional perennial-type artichoke cultivation methods are well known in the art (e.g. Ciccarelli N., Curadi M., Picciarelli P., Martelloni L., Sbrana C., Giovannetti M. "Globe artichoke as a functional food" *Mediterranean Journal of Nutrition and Metabolism* 2010 3:3 (197-201)). In traditional cultivation methods, artichoke plants are typically grown in flat fields with ditches created by repeated plowing in order to flow water and have harvest workers to walk on. Furthermore, artichoke plants are traditionally mowed at a certain time of year, e.g., a cut in May would facilitate a harvest in Fall and Spring of the following year.

Applicant sought to develop an artichoke growing system of cultivating artichoke plants as perennials such that the artichoke plants produce high yields and exhibit uniform bud production with harvest times that may also be accurately controlled or predicted. In this method, artichoke crowns are planted in a field of raised beds with a planting density of 1,700-8,000 plants/acre. The raised beds in the field have a bed width of 40-95 inches, and a bed height of 5-30 inches. The planting spacing in a row is between 20-50 inches. The artichoke plants may be mowed at any time of the year to manipulate bud production timing, in order to increase the control of harvest time.

Table 1 below outlines a summary of various aspects and characteristics of the artichoke planting and cultivation method developed by Applicant.

TABLE 1

Crown-propagated Artichoke Production Method Summary

| Aspects | Sub-aspects | Characteristics |
|---|---|---|
| Ground Preparation | | Deep tillage; several disking, chiseling and cultivator passes. |
| Bed Preparation | | Listing raised beds. Bed width 40-95 inches. |
| Plant Source | | Artichoke crowns. |
| Planting | | Mechanically or manually transplanted. In row plant spacing 20-50 inches. |
| Plants per Acre | | 1,700-8,000. |
| Fertilizing | Soil amendments before planting | If needed. |
| | Side dressing with tractor | Only early. |
| | By hand | Yes |
| | Through sprinkler | Yes. |
| | Drip | Yes. |
| Irrigation | Drip | Yes. |
| | Sprinkler | Yes. |
| | Furrow | Yes. |
| Pest Control | Pesticide spraying | Most effective, due to spacing. |
| | Slug/Snail control | Less costly than traditional perennial. |
| | Mice/Gopher control | Less costly than traditional perennial. |
| Weed Control | Mechanically | Effective due to bed width and space. |
| | By hand | Effective due to bed width and space. |
| | Herbicide by hand | Effective due to bed width and space. |
| | Herbicide mechanically | Effective due to bed width and space. |
| | Stumping | None. |
| Winter Preparation | | No plowing to create winter ditches. Tail ditches are installed at the low ends of the fields to capture and direct the flow of furrow water out and away from the field and plants. |
| Harvesting | | 1 to 15 harvest events (low harvesting cost). |
| Production Interval | | 8 months-20 years (or more). |
| Post-Harvest Plant Maintenance | | Mowing. As long as the field and plant conditions are favorable, the plants are mowed to 1 inch to 2 feet tall after each harvest interval ends, and possibly again during vegetative growth phases in order to start a new growth cycle and influence the timing of bud development. |
| Yield | | 500-1600 cartons/ac. Production of marketable buds is impacted by pest damage, frost, and air/soil temperatures. |
| Timing | | Can be planted or chopped at any time of the year to manipulate harvest interval timing. Easy to schedule. |
| Options | Organic | No. |

Example 2

Direct Seed-propagated Artichoke Planting and Cultivation Method

This example demonstrates a direct seed-propagated artichoke planting and cultivation method that may be used to provide better control of artichoke production in a calendar year, as well as allow for continued artichoke production across multiple years.

Applicant sought to develop an artichoke growing system of cultivating artichoke plants as perennials such that the artichoke plants produce high yields and exhibit uniform bud production with harvest times that may also be accurately controlled or predicted.

In this method, artichoke seeds are planted in a field of raised beds, with a planting density of 1,700-8,000 seed/acre. The raised beds in the field have a bed width of 40-95 inches, and a bed height of 5-30 inches. The planting spacing in a row is between 20-50 inches. Because these plants originate from seed, these plants have a lower disease level than traditionally planted perennial artichoke crowns.

In contrast to the regular method of growing seed-propagated artichokes as annuals, in this method, the seed-propagated plants remain in the field after a harvest cycle ends. The artichoke plants are mowed after a harvest cycle to stimulate another vegetative growth phase and harvest cycle, thus grown as perennials. Mowing may take place multiple times in a year, and may occur at any time in a year, in order to accurately control and predict harvest time.

Table 2 below outlines a summary of various aspects and characteristics of the artichoke planting and cultivation method developed by Applicant.

TABLE 2

Direct Seed-propagated Artichoke Production Method Summary

| Aspects | Sub-aspects | Characteristics |
|---|---|---|
| Ground Preparation | | Deep tillage; several disking, chiseling and cultivator passes. |
| Bed Preparation | | Listing raised beds. Bed width 40-95 inches. |
| Plant Source | | Direct field planted artichoke seed |
| Planting | | Mechanically or manually transplanted. In row plant spacing 20-50 inches. |
| Plants per Acre | | 1,700-8,000. |
| Fertilizing | Soil amendments before planting | If needed. |
| | Side dressing with tractor | Only early. |
| | By hand | Yes |
| | Through sprinkler | Yes. |
| | Drip | Yes. |
| Irrigation | Drip | Yes. |
| | Sprinkler | Yes. |
| | Furrow | Yes. |
| Pest Control | Pesticide spraying | Most effective, due to spacing. |
| | Slug/Snail control | Less costly than traditional perennial. |
| | Mice/Gopher control | Less costly than traditional perennial. |
| Weed Control | Mechanically | Effective due to bed width and space. |

TABLE 2-continued

Direct Seed-propagated Artichoke Production Method Summary

| Aspects | Sub-aspects | Characteristics |
|---|---|---|
| | By hand | Effective due to bed width and space. |
| | Herbicide by hand | Effective due to bed width and space. |
| | Herbicide mechanically | Effective due to bed width and space. |
| | Stumping | None. |
| Winter Preparation | | No plowing to create winter ditches. Tail ditches are installed at the low ends of the fields to capture and direct the flow of furrow water out and away from the field and plants. |
| Harvesting | | 1 to 15 harvest events (low harvesting cost). |
| Production Interval | | 8 months-20 years (or more). |
| Post-Harvest Plant Maintenance | | Mowing. As long as the field and plant conditions are favorable, the plants are mowed to 1 inch to 2 feet tall after each harvest interval ends, and possibly again during vegetative growth phases in order to start a new growth cycle and influence the timing of bud development. |
| Yield | | 500-1600 cartons/ac. Production of marketable buds is impacted by pest damage, frost, and air/soil temperatures. |
| Timing | | Can be planted or chopped at any time of the year to manipulate harvest interval timing. Easy to schedule. |
| Options | Organic | Yes. |

Example 3

Seed-propagated Artichoke Planting and Cultivation Method

This example demonstrates another seed-propagated artichoke planting and cultivation method that may be used to provide better control of artichoke production in a calendar year, as well as allow for continued artichoke production across multiple years.

Applicant sought to develop an artichoke growing system of cultivating artichoke plants as perennials such that the artichoke plants produce high yields and exhibit uniform bud production with harvest times that may also be accurately controlled or predicted.

Compared to the method described in Example 2, where artichoke seeds are planted directly into a field of raised beds, this Example illustrates a method of germinating artichoke seed in a greenhouse, and subsequent transplanting of the plantlets (plugs) into the field either mechanically or manually. In this method, artichoke seeds are planted in peat and vermiculite based growth medium in greenhouse, where the environment is controlled and optimized for artichoke seed germination and rooting. The artichoke seeds are grown in a germination tray for ease of subsequent transplanting. In this method, the artichoke plantlets are small enough to be amenable to mechanical transplantation into a field, in contrast to the crow-propagated perennial artichoke propagation method where crowns have to be manually planted into a field.

After about six weeks of growth in greenhouse, plantlets are transplanted onto raised beds in a commercial artichoke field, with a planting density of 1,700-8,000 seed/acre. The raised beds in the field have a bed width of 40-95 inches, and a bed height of 5-30 inches. The planting spacing in a row is between 20-50 inches. As these plants began in a greenhouse environment before planting in the field, these plants have a lower disease level than traditionally planted perennial artichoke crowns.

In contrast to the regular method of growing seed-propagated artichokes as annuals, in this method, the seed-propagated plants remain in the field after a harvest cycle ends. The artichoke plants are mowed after a harvest cycle to stimulate another vegetative growth phase and harvest cycle, thus grown as perennials. Mowing may take place multiple times in a year, and may occur at any time in a year, in order to accurately control and predict harvest time.

Table 3 below outlines a summary of various aspects and characteristics of the artichoke planting and cultivation method developed by Applicant.

TABLE 3

Seed-propagated Artichoke Production Method Summary

| Aspects | Sub-aspects | Characteristics |
|---|---|---|
| Ground Preparation | | Deep tillage; several disking, chiseling and cultivator passes. |
| Bed Preparation | | Listing raised beds. Bed width 40-95 inches. |
| Plant Source | | Artichoke seed germinated in a greenhouse. Plants transplanted to field. |
| Planting | | Mechanically or manually transplanted. In row plant spacing 20-50 inches. |
| Plants per Acre | | 1,700-8,000. |
| Fertilizing | Soil amendments before planting | If needed. |
| | Side dressing with tractor | Only early. |
| | By hand | Yes. |
| | Through sprinkler | Yes. |
| | Drip | Yes. |
| Irrigation | Drip | Yes. |
| | Sprinkler | Yes. |
| | Furrow | Yes. |
| Pest Control | Pesticide spraying | Most effective, due to spacing. |
| | Slug/Snail control | Less costly than traditional perennial. |
| | Mice/Gopher control | Less costly than traditional perennial. |
| Weed Control | Mechanically | Effective due to bed width and space. |
| | By hand | Effective due to bed width and space. |
| | Herbicide by hand | Effective due to bed width and space. |
| | Herbicide mechanically | Effective due to bed width and space. |
| | Stumping | None. |
| Winter Preparation | | No plowing to create winter ditches. Tail ditches are installed at the low ends of the fields to capture and direct the flow of furrow water out and away from the field and plants. |
| Harvesting | | 1 to 15 harvest events (low harvesting cost). |

TABLE 3-continued

Seed-propagated Artichoke Production Method Summary

| Aspects | Sub-aspects | Characteristics |
|---|---|---|
| Production Interval | | 8 months-20 years (or more). |
| Post-Harvest Plant Maintenance | | Mowing. As long as the field and plant conditions are favorable, the plants are mowed to 1 inch to 2 feet tall after each harvest interval ends, and possibly again during vegetative growth phases in order to start a new growth cycle and influence the timing of bud development. |
| Yield | | 500-1600 cartons/ac. Production of marketable buds is impacted by pest damage, frost, and air/soil temperatures. |
| Timing | | Can be planted or chopped at any time of the year to manipulate harvest interval timing. Easy to schedule. |
| Options | Organic | Yes. |

Example 4

Tissue Culture-propagated Artichoke Planting and Cultivation Method

This example demonstrates a tissue culture-propagated artichoke planting and cultivation method that may be used to provide better control of artichoke production in a calendar year, as well as allow for continued artichoke production across multiple years.

Figure 2:
FIG. 2 shows an artichoke crown that is used in traditional cultivation methods for propagating perennial artichokes. This figure illustrates the labor-intensive manual process associated with the traditional propagating methods.
Figure 5:
FIG. 5 shows the comparison of the planting material used in traditional cultivation methods (crown on the left) and the improved cultivation method (plantlet on the right). This figure illustrates the large size of the traditional planting material that renders it unamenable to machine-assisted planting. This figure also illustrates the soil lump of the traditional material that carries over potential contaminating agents into the new field.

In traditional perennial artichoke cultivation methods, perennial artichokes are reproduced asexually by rootstock division, where rooted sections of the crown (stump) of an artichoke plant are dug out of the ground, split in parts, and then transplanted by hand into a new field (FIG. 2). Plants produced by this method have lesser uniformity with respect to their morphological and physiological characteristics, due to variable diseases, pests and weeds carried over from the rootstock (FIG. 1). Additionally, rootstocks are usually too large to be planted by machine planters (FIG. 5); plants produced by this method typically grow in an irregular pattern, in a flat field, with drainage ditches installed during the fall or autumn prior to the rain season. As a result, typical yield of perennial artichokes cultivated using traditional cultivation methods is in the range of 300 to 600 cartons per acre.

Applicant sought to develop an artichoke growing system of cultivating artichoke plants as perennials such that the artichoke plants produce high yields and exhibit uniform bud production with harvest times that may also be accurately controlled or predicted.

Healthy, robust and vigorous perennial artichoke plants are selected from a perennial artichoke field. Selected artichoke plants are substantially free of contaminating agents normally present in artichoke production fields, such as weed seeds, insects, slugs, etc.

Figure 3:
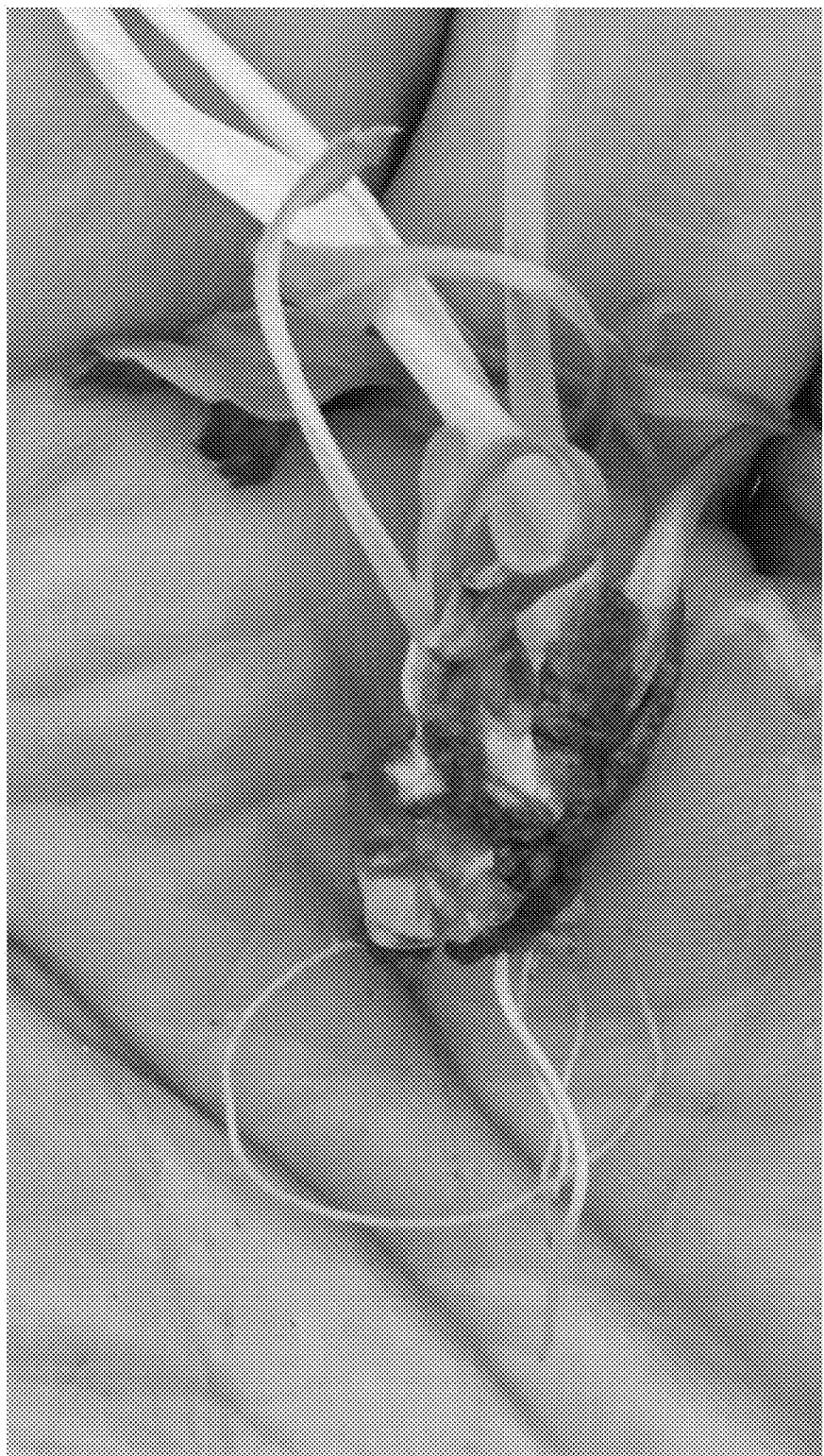
FIG. 3 shows an artichoke plant regenerated from tissue culture as part of the improved cultivation methods for cultivating perennial artichokes.

Shoot apices are excised from the selected artichoke plants, and used as primary explants to establish tissue cultures. 40 pieces of explants are plated on Murashige and Skoog (MS) agar medium (Murashige & Skoog, 1962) supplemented with 30 g/l sucrose. 1 mg/l of benzyladenine is added as a growth regulator to induce growth of axillary shoots. After four weeks, 2 mg/l of indole-3-acetic acid is added to the growth medium for root induction. After five weeks, rinse the agar off the rooted plantlets (agar plugs) and transfer them to greenhouse for hardening (FIG. 3).

Figure 4:
FIG. 4 shows a regenerated artichoke plant grown in greenhouse.

While in greenhouse, grow the regenerated plantlets in a peat and vermiculite based growth medium (FIG. 4). Plantlets are grown in 72-cell growth trays to facilitate subsequent transplantation into field.

Figure 6:
FIG. 6 shows an example of transplanting artichoke plantlets to a field using a transplanting machine. This figure illustrates the process of an operator dropping plantlets into the planter.
Figure 7:
FIG. 7 shows an artichoke field being transplanted with artichoke plantlets.

After eight weeks of growth in greenhouse, plantlets are transplanted mechanically onto raised beds in a commercial artichoke field (FIG. 6 and FIG. 7). The tissue culture-derived artichoke plants are planted such that in-row plant spacing is 36 inches. Plants are also planted on raised beds that are 80 inches in width.

As these plants began under sterile laboratory conditions, followed by a greenhouse environment before planting in the field, these plants have a lower disease level than traditionally planted perennial artichoke crowns.

The tissue culture-derived artichoke plants planted in this field are mowed at appropriate times to control the timing and production of the artichoke buds.

Figure 8:
FIG. 8 shows an artichoke field that is cultivated using improved perennial cultivation methods. This figure illustrates that the artichoke plants are tall, robust and uniform.

This artichoke cultivation method results in a production system capable of producing perennial artichoke products, throughout the production interval, according to a more predictable harvest schedule. Further, maintenance of the perennial artichoke field is significantly reduced. The uniformly planted perennial artichoke plants result in significantly easier weed and pest control as compared to traditional methods of growing artichokes as perennials. The orderly plant spacing and raised beds contribute to cultivation methods that are more precise, cost less, and are more effective than traditional methods of perennial artichoke production (FIG. 8). The yield of perennial artichokes grown with this improved method is in the range of 500 to 1600 cartons per acre.

Table 4 below outlines a summary of various aspects and characteristics of the artichoke planting and cultivation method developed by Applicant.

TABLE 4

Tissue Culture-propagated Artichoke Production Method Summary

| Aspects | Sub-aspects | Characteristics |
|---|---|---|
| Ground Preparation | | Deep tillage; several disking, chiseling and cultivator passes. |
| Bed Preparation | | Listing raised beds. Bed width 40-95 inches. |
| Plant Source | | Artichoke plant selections replicated with tissue culture. Tissue culture-derived plants rooted in a greenhouse. |
| Planting | | Mechanically or manually transplanted. In row plant spacing 20-50 inches. |
| Plants per Acre | | 1,700-8,000. |
| Fertilizing | Soil amendments before planting | If needed. |
| | Side dressing with tractor | Only early. |
| | By hand | Yes. |
| | Through sprinkler | Yes. |
| | Drip | Yes. |
| Irrigation | Drip | Yes. |
| | Sprinkler | Yes. |
| | Furrow | Yes. |

TABLE 4-continued

Tissue Culture-propagated Artichoke Production Method Summary

| Aspects | Sub-aspects | Characteristics |
|---|---|---|
| Pest Control | Pesticide spraying | Most effective, due to spacing. |
| | Slug/Snail control | Less costly than traditional perennial. |
| | Mice/Gopher control | Less costly than traditional perennial. |
| Weed Control | Mechanically | Effective due to bed width and space. |
| | By hand | Effective due to bed width and space. |
| | Herbicide by hand | Effective due to bed width and space. |
| | Herbicide mechanically | Effective due to bed width and space. |
| | Stumping | None. |
| Winter Preparation | | No plowing to create winter ditches. |
| | | Tail ditches are installed at the low ends of the fields to capture and direct the flow of furrow water out and away from the field and plants. |
| Harvesting | | 1 to 15 harvest events (low harvesting cost). |
| Production Interval | | 8 months-20 years (or more). |
| Post-Harvest Plant Maintenance | | Mowing. As long as the field and plant conditions are favorable, the plants are mowed to 1 inch to 2 feet tall after each harvest interval ends, and possibly again during vegetative growth phases in order to start a new growth cycle and influence the timing of bud development. |
| Yield | | 500-1600 cartons/ac. Production of marketable buds is impacted by pest damage, frost, and air/soil temperatures. |
| Timing | | Can be planted or chopped at any time of the year to manipulate harvest interval timing. Easy to schedule. |
| Options | Organic | Yes. |

Deposit Information

A deposit of the plant tissue cultures disclosed in this invention is maintained by Luis A Scattini & Sons LP, having an address at 55 East San Joaquin Street, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the deposit will be irrevocably removed by affording access to a deposit of at least 25 cryopreserved vials of plant tissue cultures made according to the Budapest Treaty in the American Type Culture Collection, (ATCC), ATCC Patent Depository, 10801 University Boulevard, Manassas, Va., 20110, USA.

At least 25 cryopreserved vials of the plant tissue cultures disclosed in the invention were deposited on DATE according to the Budapest Treaty in the American Type Culture Collection (ATCC), ATCC Patent Depository, 10801 University Boulevard, Manassas, Va., 20110, USA. The deposit has been assigned ATCC number X. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the deposit will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

What is claimed is:

1. A method for cultivating artichoke *Cynara cardunculus* plants as perennials, the method comprising:
   growing artichoke plants in a field on raised beds for more than one harvest interval to produce a field of artichoke plants, wherein the artichoke plants comprise a vegetative portion and wherein the harvest interval comprises multiple harvest events; and
   mowing the vegetative portion of the artichoke plants multiple times after a first harvest interval and before the beginning of a second and each subsequent harvest interval,
   wherein the artichoke plant density from about 1,700 to about 8,000 artichoke plants per acre.

2. The method of claim 1, wherein each of the artichoke plants is grown from an artichoke crown.

3. The method of claim 1, wherein each of the artichoke plants is grown from an artichoke seed.

4. The method of claim 1, wherein each of the artichoke plants is grown from an artichoke plantlet germinated from an artichoke seed.

5. The method of claim 4, further comprising growing the artichoke plantlets in a greenhouse for about 6 weeks.

6. The method of claim 1, wherein each of the artichoke plants is grown from an artichoke plantlet regenerated from artichoke tissue culture.

7. The method of claim 6, further comprising growing the artichoke plantlets in greenhouse for about 8 weeks in a growth medium comprising peat and vermiculite.

8. The method of claim 6, wherein the tissue culture is originated from a plant part selected from the group consisting of leaf, anther, pistil, stem, petiole, shoot, shoot tip, root, root tip, fruit, seed, flower, cotyledon, hypocotyl, embryo and meristematic cell.

9. The method of claim 1, wherein the raised beds comprise a width from about 40 inches to about 95 inches.

10. The method of claim 1, wherein the raised beds comprise a height from about 2.5 inches to about 30 inches.

11. The method of claim 1, wherein the artichoke plants in the raised beds are spaced from about 20 inches to about 50 inches apart.

12. The method of claim 1, wherein the artichoke plants are grown in the field of raised beds for multiple harvest intervals and vegetative growth phases.

13. The method of claim 1, wherein the mowing takes place in any month in a year.

14. The method of claim 1, wherein mowing comprises mowing the artichoke plants to 1 inch to 2 feet tall after a harvest interval ends.

15. The method of claim 1, further comprising harvesting artichoke buds from the artichoke plants.

* * * * *